United States Patent [19]

Abdel-Monem

[11] Patent Number: 4,678,854

[45] Date of Patent: Jul. 7, 1987

[54] COBALT COMPLEXES AND THEIR USE AS NUTRITIONAL SUPPLEMENTS

[75] Inventor: Mahmoud M. Abdel-Monem, St. Paul, Minn.

[73] Assignee: Zinpro Corporation, Chaska, Minn.

[21] Appl. No.: 748,851

[22] Filed: Nov. 25, 1986

[51] Int. Cl.$^4$ ............................................... C07F 15/06
[52] U.S. Cl. .................................... 556/149; 556/147; 260/414; 426/74
[58] Field of Search .................. 556/147, 149; 260/414

[56] References Cited

U.S. PATENT DOCUMENTS

| | | | |
|---|---|---|---|
| 1,452,478 | 4/1923 | Ellis ...................................... | 556/149 |
| 2,097,235 | 10/1937 | Schmidt et al. ................. | 556/149 X |
| 2,474,989 | 7/1949 | Schnider .......................... | 556/149 X |
| 2,688,032 | 8/1954 | Kopelman et al. ................. | 556/149 |
| 2,735,866 | 2/1956 | Clevenot .......................... | 556/149 X |
| 2,909,408 | 10/1959 | West et al. ....................... | 556/147 X |
| 3,091,626 | 5/1963 | Carlson .............................. | 556/147 |
| 3,459,677 | 8/1969 | Robeson .......................... | 556/149 X |
| 3,925,433 | 12/1975 | Abdel-Monem et al. . | |
| 3,941,818 | 3/1976 | Abdel-Monem . | |
| 3,950,372 | 4/1976 | Abdel-Monem . | |
| 3,974,197 | 8/1976 | Parliment ......................... | 556/147 X |
| 4,021,569 | 5/1977 | Abdel-Monem . | |
| 4,039,681 | 8/1977 | Abdel-Monem . | |
| 4,067,994 | 1/1978 | Anderson et al. . | |

*Primary Examiner*—Helen M. S. Sneed
*Attorney, Agent, or Firm*—Zarley, McKee, Thomte, Voorhees & Sease

[57] ABSTRACT

Complex salts of cobalt useful for nutritional supplementation to provide cobalt in a form which effectively increases the bioavailability of cobalt, assuring adequate dietary requirement for growth and production of vitamin $B_{12}$ by microorganisms present in the gut.

5 Claims, No Drawings

COBALT COMPLEXES AND THEIR USE AS NUTRITIONAL SUPPLEMENTS

BACKGROUND OF THE INVENTION

Vitamin $B_{12}$ is unique among the vitamins in that it contains not only an organic molecule, but also the essential trace element cobalt. Vitamin $B_{12}$ is not made by either plants or animals and can be synthesized by only a few species of microorganisms. Bacteria in the human intestinal tract can make enough Vitamin $B_{12}$ for normal daily requirements from inorganic cobalt salts in the diet. Vitamin $B_{12}$ is also made in large amounts by rich populations of bacteria in the rumen of ruminant animals and in the cecum of other herbivorous species.

Vitamin $B_{12}$ participates in many biochemical processes that are essential for life. It acts as a co-enzyme for several enzymes which catalyze the shift of a hydrogen atom from one carbon atom to an adjacent one in exchange for an alkyl, carboxyl, hydroxyl or amino groups. Deficiency of Vitamin $B_{12}$ results in the development of the serious disease pernicious anemia. Pernicious anemia, as the name implies, involves a low concentration of hemoglobin resulting from the condition, but the effects also include serious disturbances of the central nervous system that may result in abnormal sensations, motion, and in humans, thought.

Pernicious anemia is usually not due to a dietary deficiency of Vitamin $B_{12}$ but rather a failure to absorb the vitamin from the intestine because of deficient secretion of the "intrinsic factor" in the stomach. Put another way, it is a genetic defect of the stomach rather than a dietary deficiency disease. The absorption of the dietary cobalamins depends upon the formation by the gastric mucosa of a carbohydrate rich protein, known as the "intrinsic factor". It is a glycol protein which is required for Vitamin $B_{12}$ absorption. Animals with pernicious anemia do not make this protein, and thus are deficient in the intrinsic factor.

In most animals, the cobalt content of the diet is sufficient for the production of the daily requirement of Vitamin $B_{12}$. However, ruminant animals, such as cattle, represent a special case because they have a great need for dietary cobalt. Dietary cobalt is essential for the growth and functioning of the rumen microorganisms. The optimal dietary requirements of cobalt for growth and production of Vitamin $B_{12}$ by these microorganisms is not known for certain, but an amount of from about 0.5 to about 1.0 milligrams per kilogram of dry matter has been suggested from various studies. Therefore, the diet must contain sufficient cobalt to insure the optimal growth of rumen bacteria. Indeed, supplemetation of poor straw diets with cobalt alone, or cobalt and copper, resulted in significant increases in the overall digestability of crude fiber as well as cellulose degradation. Furthermore, in the rumen, the different bacterial species cooperate to degrade major plant components, particularly cellulose, to D-glucose which is further degraded to lactate, acetate, propionate, and butyrate. In contrast to other mammalian species, in cattle only a few grams of glucose passes from the intestine into the blood stream in a 24 hour period. Nevertheless, cattle need glucose not only to supply energy to the brain and other organs, but also as a source of milk sugar (lactose) in lactating cows. Glucose is formed in the liver from lactate and propionate by gluconeogenesis. The conversion of propionate to glucose requires an enzyme containing Vitamin $B_{12}$. Hence, the requirement for Vitamin $B_{12}$ is high in cattle, especially lactating cows.

Only a fraction of the ingested cobalt is utilized by the gut microorganisms for the production of Vitamin $B_{12}$. It appears that cobalt is transported into bacterial cells by the same transport system as magnesium, and that its uptake depends upon metabolic energy. Thus, it can be seen that it is imperative that the diet, and especially the diet of ruminants, contain an adequate source of cobalt. It is also imperative that cobalt be in a bioavailable form such that it is available for growth and production of Vitamin $B_{12}$ by the gut microorganisms.

It is therefore a primary objective of the present invention to provide a highly effective bioavailable form of cobalt in convenient water soluble salt form which is available for use as a feed additive in animal nutrition, especially ruminant animals.

Another important objective of the present invention is the preparation of novel salts of cobalt in which the cobalt is in a form that can readily be absorbed after ingestion by gut microorganisms and utilized in the production of Vitamin $B_{12}$.

Yet another objective of the present invention is the preparation of forms of cobalt which are stable, readily soluble in water, and easily and economically manufactured.

An even further objective of the present invention is to provide a method of nutritional supplementation for animals, especially ruminant animals, to assure adequate dietary requirement for growth and production of Vitamin $B_{12}$ by microorganisms present in the gut of ruminant animals.

A yet further objective is to provide an easy, simple and direct synthesis route for bioavailable forms of cobalt useful as feed additives in animal nutrition.

A still further objective of the present invention is to provide certain complexed salts of cobalt and certain alpha hydroxy organic acids, such as glyceric acid having coordination bonds formed between the cobalt cation and the alpha hydroxy group of the acid, in addition to the electrostatic attraction between the cation and the carboxyl ions.

The method of accomplishing these as well as other objectives of the invention will become apparent from the detailed description which follows hereinafter.

SUMMARY OF THE INVENTION

This invention relates to the preparation of novel cobalt complexes which have the following general formula:

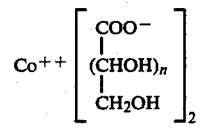

wherein n is a whole integer and equals from 1 to 5. When n=1 the acid is glyceric acid and when n=5, it is glucoheptonic acid. When n=2, the acid moiety is from erythronic or threonic acid. When n=3, the acid is arabinonic, ribonic or xylonic. When n=4, the acid is gluconic acid. These compounds, it is believed because of a complex formed between the cobalt cation and the alpha hydroxy acid, are in a form that is readily absorbed by the gut bacteria and utilized for the production of Vitamin $B_{12}$. These complexes thus function as a readily available source of cobalt for dietary supplementation, assuring necessary cobalt absorption by the gut bacteria adequate to growth and production of Vitamin $B_{12}$, which in turn is then available for use by the host animal, such as a ruminant animal, especially cattle.

The invention also relates to a new, simple and economically feasible process for making the above described compounds, and to their use for assuring adequate dietery requirement for growth and production of Vitamin $B_{12}$ by microorganisms present in the gut.

DETAILED DESCRIPTION OF THE INVENTION

The compounds of the present invention can be described as cobalt complex salts between the cobalt cation and certain alpha hydroxy organic acids of the general formula:

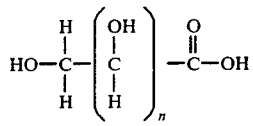

wherein n equals from 1 to 5. The preferred acid is when n equals 5, glucoheptonic acid. However, n should not increase substantially beyond 5 because compounds where n is greater than 5 are not readily available and are not commercially feasible.

It is also important to note that the compounds of this invention are cobalt complexes in which coordination bonds are formed between the cobalt cation and the alpha hydroxyl group of the acid, in addition to the electrostatic attraction between the cation and the carboxyl anions. This complex salt involving both coordination bonds and electrostatic attraction, seems to enhance the bioavailability of the cobalt. The general formula of these complexes, illustrating both the coordination bond and the electrostatic attraction, can be represented as follows:

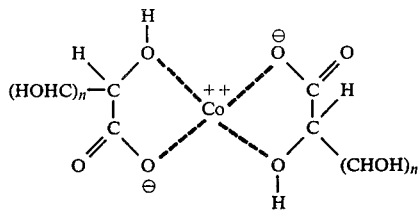

A simple and economically feasible process of preparing these cobalt complexes has been developed. For the sake of brevity, only examples of the preparation of a cobalt glucoheptonate and the cobalt gluconate will be described. However, these methods can easily be applied to the preparation of other cobalt complexes of this invention, such as the cobalt glycerate, erythronate and xylonate.

In accord with the process of this invention, a solution of cobalt sulfate whether in an anhydrous form or in a hydrated form is mixed with an equimolar amount of calcium gluconate or calcium glucoheptonate. The copious precipitate of calcium sulfate which is formed is filtered. The product, cobalt gluconate or cobalt glucoheptonate, can be conveniently obtained from the filtrate by the addition of an organic solvent such as isopropyl alcohol, acetone, or ethyl alcohol. Alternatively, the filtrate could be dried using conventional drying methods such as hot air oven, spray drying, freeze drying or evaporation under reduced pressure.

The same complexes may be obtained by mixing one molar equivalent of cobalt chloride with a concentrated aqueous solution of two molar equivalents of sodium gluconate or sodium glucoheptonate. The mixture is treated with acetone (10x). The supernatant is decanted from the heavy precipitate formed. The supernatant may have a purple color due to the solubility of unreacted cobalt chloride in the aqueous acetone solvent. The precipitate is treated with acetone and mixed thoroughly. The acetone supernatant is discarded. The addition of acetone is repeated until the precipitate is in a crystalline form and the acetone supernatant is colorless. The crystalline precipitate is a mixture of the cobalt complex and sodium chloride as determined by elemental analysis.

Another convenient method for obtaining the cobalt complexes involves the careful addition of powdered cobalt carbonate to a stirred solution of, for example, gluconic acid or glycoheptonic acid. Carbon dioxide gas is formed in this reaction, hence vigorous effervescence takes place and must be controlled by limiting the amount of cobalt carbonate added. Cobalt gluconate or cobalt glucoheptonate can be obtained from the clear deep red solution by the addition of an organic solvent or the filtrate can be dried using conventional drying methods.

The level of addition of the cobalt alpha hydroxy acid complexes of this invention for use as a feed supplement, especially for ruminants, can vary over a wide range. Preferably the level of addition is such to provide dietary intake of cobalt from about 0.2 parts per million to about 2.0 parts per million, and most preferably about 1.0 parts per million. Experimental data has shown that these levels are satisfactorily achieved when the amount of the complex salt cobalt glucoheptonate, added to the animal feed, is from about 0.1 g per head of cattle per day to about 1.0 g per head of cattle per day, preferably 0.6 g per head of cattle per day. It should, however, be understood that other levels of addition can be utilized and that the precise level of addition is not in fact critical, it being adjusted for the conditions of the animals being treated with the nutritional supplement.

Importantly, one of the distinct advantages of the compounds of the present invention is that they are crystalline water soluble compounds easily processible and size reducible to a powder for use in a convenient feed supplement form. In other words, their physical form is one which is easily mixable with typical ruminant animal feeds.

The following examples are offered to further illustrate, but not limit, the preparation of the compounds of this invention.

EXAMPLE 1

A solution of hydrated cobalt sulfate ($CoSO_4.6H_2O$, 28 g, 0.105 mole) in water (50 ml) was heated to 80° C. Calcium gluconate (45 g, 0.105 mole) was added portionwise with stirring. The mixture was heated on a steam bath for five minutes and cooled to room temperature. The copious precipitate of calcium sulfate was filtered and washed with three successive portions of 10 ml of water. The filtrate was concentrated under reduced pressure. The residue was treated with 20 ml of absolute ethanol and concentrated in vacuo. The residue (45 g, 95.7 percent yield) contained 13.0 percent cobalt (theory 13.1 percent). The residue was readily soluble in water to give a deep red solution.

EXAMPLE 2

Cobalt carbonate (12.0 g, 0.1 mole) was carefully added to a continuously stirred solution of glucoheptonic acid (45.2 g, 0.2 mole) in 200 ml of water. After the addition of solids was complete, the mixture was stirred for additional 15 minutes and filtered. The filtrate was concentrated under reduced pressure at a temperature of 40° C. The residue was treated with 20 ml of absolute ethanol and concentrated in vacuo. The dry residue weighed 50.4 g (yield 99 percent) and contained 11.3 percent cobalt (theory 11.6 percent).

EXAMPLE 3

A solution of sodium glucoheptonate (50 g, 0.2 mole) in water (50 ml) was heated to 80° C. Hydrated cobalt chloride ($CoCl_2.6H_2O$, 24 g, 0.1 mole) was slowly added. The solution was stirred at 80° C. for additional 15 minutes and filtered. The filtrate was treated with 200 ml of acetone. The dark blue supernatant was carefully decanted. The residue was treated with 100 ml of acetone and mixed thoroughly. The colorless supernatant was decanted and the residue was treated with 100 ml of acetone. The crystalline solid was filtered. The solid weighed 61.0 g and contained 9.5 percent cobalt (theory 9.3 percent).

EXAMPLE 4

Nutritional Bioavailability of Cobalt From Cobalt Glucoheptonate

The effect of cobalt supplementation on the ability of standard diet to serve as substrate for microbial metabolism was studied using continuous culture in vitro fermenters. The continuous culture was designed to simulate in vivo rumen results by maintaining rumen microbes under similar environmental conditions found in the rumen. Fermenter flasks with overflow tubes were used. The flask was filled with rumen fluid at pH 6.5 and placed in a water bath at 39° C. Artificial saliva infused continuously into the flask via a piston drive pump at the rate of 0.1 hr.$^{-1}$ (10% of total rumen volume was replaced per hour). Diets were provided continuously via an automatic feeding system at the rate of 7.5% dry matter of total fermenter volume per 24 hr. The solids dilution rate was 0.05 hr.$^{-1}$ (5% of it was added every hour and mean rumen retention time of 20 hour). The contents of the fermenter were mixed at 250-300 rpm and nitrogen gas was purged at the rate of 40 mL/min.

Effluents from the culture flasks were collected in a 4-liter container which was maintained in a water bath at 2°–4° C. to inhibit further microbial enzyme activity. Saturated mercuric chloride was also added to the effluent at the rate of 1 mL per 50 mL effluent. Daily effluent was sampled by aspiration after homogenization. The first 5 days of the experiment served as an equilibration period followed by a 3 day sampling period. On the last day of each experimental period, cultures from the fermenter fluids were used to separate the bacterial population by filteration and differential centrifugation. Four diets were used and the above procedure was replicated six times for each diet. One diet contained no additional cobalt. The other three contained additional 1 ppm of cobalt from cobalt glucoheptonate, commercial organic cobalt complex and cobalt sulfate. The effluents were analyzed for digestibility of dry matter, organic matter, neutral detergent, acid detergent, hemicellulose, cellulose and lignin.

The bioavailability of cobalt can be assessed from the percent digestibility of the diet. The higher the bioavailability of cobalt, the higher the percent digestibility of the diet.

TABLE I

| | Results Percent Digestibility | | | |
|---|---|---|---|---|
| | Control | Cobalt Glucoheptonate | Organic Cobalt | Cobalt Sulfate |
| Dry matter | 26.0 | 29.7 | 26.7 | 25.8 |
| Organic matter | 32.6 | 34.5 | 33.2 | 32.1 |
| Neutral detergent fibers | 28.9 | 32.8 | 27.8 | 29.0 |
| Acid detergent fibers | 35.8 | 41.0 | 34.7 | 38.5 |
| Hemicellulose fibers | 21.9 | 24.9 | 26.0 | 21.5 |
| Cellulose fibers | 39.1 | 44.1 | 38.0 | 40.7 |
| Lignin fibers | 26.0 | 31.6 | 29.7 | 32.3 |

It can be seen that the cobalt form of the invention provided the highest bioavailability.

What is claimed is:

1. Cobalt complex salts of the formula:

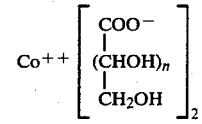

wherein n is from 1 to 5.

2. The complex salts of claim 1 wherein n=5.

3. The salts of claim 1 wherein said salt is in solid form.

4. The salts of claim 1 wherein said salt is in a finely divided state, suitable for use as a feed supplement.

5. Cobalt glucoheptonate.

* * * * *